(12) United States Patent
Harttig et al.

(10) Patent No.: US 6,545,143 B1
(45) Date of Patent: Apr. 8, 2003

(54) MAGNETIC PARTICLES FOR PURIFYING NUCLEIC ACIDS

(75) Inventors: Herbert Harttig, Altrip (DE); Michael Riedling, St. Ingbert (DE); Martin Mennig, Quierschied (DE); Helmut Schmidt, Saarbrüchen-Güdingen (DE)

(73) Assignee: Roche Diagnostics, GmbH, Mannheim (DE)

( * ) Notice: Subject to any disclaimer, the term of this patent is extended or adjusted under 35 U.S.C. 154(b) by 0 days.

(21) Appl. No.: 09/856,737

(22) PCT Filed: Nov. 23, 1999

(86) PCT No.: PCT/EP99/08996

§ 371 (c)(1),
(2), (4) Date: Jul. 12, 2001

(87) PCT Pub. No.: WO00/32762

PCT Pub. Date: Jun. 8, 2000

(30) Foreign Application Priority Data

Nov. 30, 1998 (DE) .......................................... 198 54 973
Nov. 30, 1998 (DE) .......................................... 198 55 259

(51) Int. Cl.$^7$ .............................................. C07H 21/04
(52) U.S. Cl. ................. 536/25.4; 106/426; 428/402.34; 428/404; 428/406
(58) Field of Search ...................... 106/426; 428/402.24, 428/404, 406; 536/25.4

(56) References Cited

U.S. PATENT DOCUMENTS

| 5,990,479 | A | * | 11/1999 | Weiss et al. ................. 250/307 |
| 6,136,083 | A | * | 10/2000 | Schmidt et al. ............. 106/403 |
| 6,255,477 | B1 | * | 7/2001 | Kleiber et al. ............. 536/25.4 |
| 6,274,386 | B1 | | 8/2001 | Harttig |

FOREIGN PATENT DOCUMENTS

| DE | 195 20 964 A1 | * | 12/1996 |
| DE | 195 37 985 A1 | * | 4/1997 |
| EP | 0 811 694 | | 10/1997 |
| WO | WO 96/41811 | | 12/1996 |
| WO | WO 96/41840 | | 12/1996 |
| WO | WO 00/32762 | | 11/1999 |

* cited by examiner

Primary Examiner—James Ketter
(74) Attorney, Agent, or Firm—Charles M. Doyle; George C. Jen; Pennie & Edmonds, LLP

(57) ABSTRACT

Preparations of particles having a glass surface, wherein more than 75% by weight of these particles have a particle size between 0.5 μm and 15 μm and a glass surface which contains between 2 and 6 mole % zinc oxide, have proven to be particularly advantageous in processes for the purification of nucleic acids. This in particular results in an increased nucleic acid yield.

14 Claims, No Drawings

MAGNETIC PARTICLES FOR PURIFYING NUCLEIC ACIDS

The application concerns a preparation of particles having a glass surface, a process for producing such a preparation and a process for purifying nucleic acids with the aid of this preparation.

Nucleic acids have recently become more and more the focus of interest for medical diagnostics. Numerous detection methods have now been developed in which the presence or absence of certain nucleic acids is used as an indication for a disease. These include for example tests for infectious organisms e.g. for viruses or bacteria in body fluids and also the detection of mutations in genomic nucleic acids e.g. in oncology. However, nucleic acids are usually present at very low concentrations in the sample material. Hence various methods have been developed for isolating nucleic acids from other sample components such as proteins or other cellular components some of which interfere with the subsequent detection methods. Some of these methods utilize capture probes bound to solid phases that can hybridize with the nucleic acids to be separated and retain these on the solid phase while the other sample components are removed. Such a method is described for example in EP-B-0 305 399. However, a disadvantage of these methods is that they are each only suitable for purifying nucleic acids having a very special nucleotide sequence.

A process for isolating nucleic acids with the aid of magnetic particles composed of cellulose and iron oxide is described in WO 91/12079 in which the particle size is stated to be between 1 and 10 $\mu$m. These particles do not contain a glass surface and are only suitable for an isolation in which the nucleic acids are precipitated. However, the aggregation process also entraps many sample components which interfere with subsequent process steps.

EP-B-0389 063 proposes a process in which the sample is mixed with a mixture of a chaotropic guanidinium salt and silica particles. Under these conditions the binding of the nucleic acids to the silica surface is relatively independent of the sequence. The other sample components can be removed by washing and the nucleic acids can be subsequently eluted.

Magnetic particles having an essentially pore-free glass surface are described in WO 96/41811 for the sequence-independent purification of nucleic acids. The particles used in this case have a core which preferably contains magnetite as a magnetic material and they preferably have a particle size between 10 and 60 $\mu$m. Magnetite exhibits hard magnetic properties in crystals larger than ca. 30 to 50 nm. Permanent magnetism is induced by an external magnetic field. Particles having such hard magnetic cores have the properties of a small permanent magnet after their first exposure to an external magnetic field. In suspensions such particles attract one another and form larger units. Under the influence of an external field of gravity these large units sediment more rapidly than the individual particles. This is disadvantageous since long periods of incubation require frequent redispersing.

Pigments are described in WO 96/41840 which have a glass surface with a thickness of at least 0.8 $\mu$m. Zinc compounds are also proposed as a glass forming component. Pigment particles are formed in this process having a particle size of preferably 2 to 20 $\mu$m.

It has now turned out that in the previously described processes for the production of particles using a sol-gel process in which core particles having a specified size are coated with a gel and subsequently a compression takes place to form a glass surface, a large proportion of particles are formed which do not contain core particles. Nucleic acid detection methods carried out using such preparations either result in large losses of nucleic acids or the fines have to be laboriously separated in order to increase the yield. The object of the present invention was to completely or partially improve the present state of the art and in particular to produce particles having a relatively narrow particle size distribution and to further increase the yield in nucleic acid purifications, or/and to provide particles for nucleic acid purification which, even after exposure to an external magnetic field, only have a very low tendency to aggregate and sediment in a gravitational field just as slowly as particles that have never been exposed to a magnetic field.

The invention concerns a preparation containing particles having a glass surface wherein more than 75% by weight of these particles have a particle size between 0.5 and 15 $\mu$m.

Further subject matters of the invention are a process for producing a preparation of particles containing a core coated with a gel layer or a glass layer and a process for purifying nucleic acids with the aid of the preparation according to the invention.

A further subject matter of the invention is a process for producing particles and a preparation of particles having a superparamagnetic core.

The invention additionally concerns a process for producing particles and a preparation of particles having a magnetic and preferably a soft magnetic metallic core.

Solid materials having a small diameter are referred to as particles by a person skilled in the art. These particles preferably have an essentially spherical surface. However, platelet-shaped and filamentary particles having the dimensions stated below are also to be understood as particles. In order to be particularly suitable for purifying nucleic acids, it is desirable that the particles have a core (pigment part) which is preferably magnetic and is coated with a layer of glass. Such cores preferably contain metal oxides such as aluminium oxide, iron oxide, chromium oxide, copper oxide, manganese oxide, lead oxide, tin oxide, titanium oxide, zinc oxide and zirconium oxide or metals such as Fe, Cr, Ni or magnetic alloys. The composition of this core is less important for the function of the particles according to the invention since the core is coated with a glass surface and hence the core does not come into direct contact with the sample from which it is intended to isolate the nucleic acid. Such cores are commercially available. If the core contains $Fe_3O_4$ (magnetite) or $Fe_2O_3$ (maghemite) or Fe or Cr or Ni or magnetic alloys, then these cores are magnetic.

Suitable materials referred to as being soft magnetic are metals based on the pure elements Fe, Ni, Cr and alloys thereof preferably based on Ni. Examples of such alloys are known under the name permalloy. They are composed of 70 to 80% Ni with additives of Cr, Cu and Mo. Particles consisting of magnetically soft material do not attract one another or only to a negligible extent in the absence of an external magnetic field.

Finely-dispersed metal powders are very reactive. There is a risk of self-ignition in air, they are pyrophoric. Hence it was very surprising that such finely dispersed metal particles could be coated with a glass layer by a sol-gel process without significantly changing the magnetic properties. Carbonyl iron powder is particularly preferably used as a metal powder and types thereof that have been reduced in $H_2$ have particularly favourable magnetic properties. Carbonyl iron whiskers have particularly favourable properties.

Metal powders preferably have a particle size between 10 nm and 100 $\mu$m and particularly preferably between 200 nm and 8 $\mu$m.

A glass surface in the sense of the present invention is composed of an amorphous material containing silicon. In addition to silicon oxide the glass preferably contains one or several of the following components (in mole %):

$B_2O_3$ (0–30%), $Al_2O_3$ (0–20%), CaO (0–20%), BaO (0–10%), $K_2O$ (0–20%), $Na_2O$ (0–20%), MgO (0–18%), $Pb_2O_3$ (0–15%),

ZnO (0–6%).

A number of other oxides can also be present in small amounts of 0–5% such as e.g. $Na_2O$, $Mn_2O_3$, $TiO_2$, $As_2O_3$, $Fe_2O_3$, CuO, $ZrO_2$, CoO etc. Surfaces having a composition of $SiO_2$, $B_2O_3$, $Al_2O_3$, CaO, $K_2O$ and ZnO have proven to be particularly effective. Boron silicate glasses that are particularly advantageous with regard to the yield of nucleic acids have a zinc oxide content of 2–6, preferably of ca. 4 mole %. The glass layer is particularly preferably composed of 68–79 mole % $SiO_2$, 15–5 mole % $B_2O_3$, 6–2.5 mole % total amount of $K_2O$ and $Na_2O$, 4–1 mole % CaO, 8–2 mole % $Al_2O_3$, 6–2 mole % ZnO. Glasses are particularly preferred in the sense of the invention which have been formed by the so-called gel-sol process and subsequent drying and compression of the layer that forms. The essential aspects of this process are known and have been described for example in C. J. Brinker, G. W. Scherer "Sol Gel science—The physics and chemistry of Sol Gel Processing", Academic Press Inc. 1990 and Sol-Gel Optics, Processing and Applications Lisa C. Klein Ed. Kluwer Academic Publishers 1994 page 450 ff and in DE-A-1941191, DE-A-3719339, DE-A-4117041 and DE-A-4217432. In the gel-sol process alkoxides of network-forming components e.g. $SiO_2$, $B_2O_3$, $Al_2O_3$, $TiO_2$, $ZrO_2$ and ZnO are added together with oxides and salts of other components e.g. in an alcoholic solution and hydrolysed.

The addition of water starts the hydrolysis of the starting components. The reaction proceeds relatively rapidly since the alkali ions have a catalytic effect on the rate of hydrolysis of the silicic acid ester. After gel formation is completed, the gel can be dried and compressed to form a glass by a thermal process.

The quantity ratio of sol to pigment has a considerable influence on the yield of the magnetic pigment according to the invention. The constraints are that the amount of pigment has to be low enough to allow a material to form that can still be pumped and sprayed. If the amount of pigment is too low, the proportion of fine material e.g. non-magnetic material becomes too large and interferes. Quantity ratios of 10 to 45 g pigment/100 ml sol have been found to be expedient with regard to the pigment yield.

The slurry is preferably sprayed through a nozzle to form a powder and the aerosol is dried on a falling path. The nozzle is preferably heated to accelerate the drying of the slurry. The nozzle temperature is preferably ca. 120 to 250° C. independent of the geometry of the nozzle. A compromise must be found between an adequate rate of evaporation and avoidance of spattering.

The compression temperature should be selected to be as high as possible with regard to yield. However, if it is too high, the particles agglutinate and agglomerates form which should be removed by sieving. But addition of zinc to the layer surprisingly increases the melting point and it is thus possible to use a higher compression temperature (between 710 and 800° C.). The after treatment in air leads to a loss of the magnetic properties if the temperature is too high which is why excessive temperatures should be avoided. When zinc is added it is also possible to use other temperatures in this case (preferably between 150 and 250° C.).

Within the scope of the present invention it has turned out that magnetic cores can be used in the process described in WO 96/41811 which are very much smaller. In particular it turned out that it is possible to use cores on a nanoscale e.g. magnetite having a crystal size of less than 50 nm, preferably less than 30 nm. The lower limit of the core size results from the handling properties of the cores and in particular their tendency to form aggregates. The cores are preferably larger than 5 nm, particularly preferably larger than 7 nm. The magnetic properties of the nanoscale cores is referred to as superparamagnetic. The particles that are obtained sediment rapidly when exposed to an external magnetic field. After redispersion their sedimentation rate in a gravitational field do not differ from their sedimentation rate in a gravitational field before exposure to the external magnetic field. This is advantageous since it enables longer incubation times in suspension without having to remix and resuspend.

In order to produce a preparation according to the invention a preparation of core particles in which more than 75% by weight of the core particles have a particle size between somewhat less than 0.5 and somewhat less than 15 $\mu$m is used in a sol/gel process. The core particles must be smaller than the glass-coated particles to the extent of the thickness of the glass layer. After the inventive process the glass layer will be between 5 nm and 1 $\mu$m thick depending on the selected conditions such as the ratio of gel to core particles. On average the glass layer should be between 0.2 and 0.3 $\mu$m thick.

A preparation is particularly preferred which contains particles having a glass surface in which more than 75% by weight of these particles have a particle size between 2 and 15 $\mu$m. The proportion of particles with the defined particle size is particularly preferably more than 90% by weight.

Magnetic core particles are particularly preferably used. An advantage of the preparation according to the invention is that preferably more than 95% by weight of the particles having a particle size between 0.5 and 15 $\mu$m, preferably between 2 and 15 $\mu$m are magnetic. This means that the proportion of particles that do not contain cores is drastically reduced in comparison to the known processes. This can be recognized by the fact that only a few non-magnetic particles are present. This means that it is practically no longer necessary to separate the non-magnetic particles from the magnetic particles before using the preparation in processes to purify nucleic acids. This simplifies the production process.

The preparation according to the invention can be additionally characterized in that preferably less than 50% of the particles have a particle size of less than 2 $\mu$m. Consequently there is a substantial reduction in the non-magnetic fine fraction which has a relatively high proportion in particles of small sizes. Particularly preferably less than 2% of the particles have a particle size of less than 0.5 $\mu$m.

Preferably no more than 10% and particularly preferably between 10 and 40% of the particles of the preparation have a particle size of more than 10 $\mu$m.

In addition to the particles according to the invention the inventive preparation can also contain other non-glass containing components such as buffer substances or a suspending agent e.g. water or alcoholic solutions of water.

The glass layer of the particles of the inventive preparation preferably contains between 2 and 6 mole %, particularly preferably 4 mole % zinc oxide. This can be achieved by having an amount of zinc oxide in the solid sol mass of this order of magnitude compared to the amounts of the other solid components. The proportion of zinc oxide increases as the amount of boron oxide decreases especially when the preparation is heated for long periods since boron oxide is already volatile under the production conditions.

Particles having a glass layer in which the proportion of zinc oxide is between 2 and 6 mole % have proven to be particularly effective for purifying nucleic acids. The yield of nucleic acids was in some cases increased by 50% compared to the same glass layer without zinc oxide.

Another subject matter of the invention is a process for producing a preparation of particles having a core coated with a gel layer that contains less than 5% by weight particles without cores comprising the steps suspending core particles in a sol using a core particle preparation and spray drying the suspension to form a gel wherein the core particle preparation contains 75% by weight particles with a particle size between 0.5 and 15 µm, preferably between 2 and 15 µm.

Reference is made to the descriptions in the prior art with regard to carrying out the gel/sol process which is used by the production process according to the invention. The main difference between the invention and the prior art is the use of a particular core particle preparation which enables production of a preparation containing less than 5% by weight particles without cores. A process has proven to be particularly advantageous in which firstly a sol is prepared from tetraalkyl orthosilicates, alkyl borates, aluminium alcoholates and alkali alcoholates in ethanol and this mixture is heated with calcium. Subsequently the mixture is hydrolysed by adding water. Core particles are added in a solid form to the sol formed in this manner and are suspended preferably with ultrasound. Subsequently the suspension is atomized to form a gel in a spray drying process in which the nozzle is heated and in which mainly particles are formed containing between 1 and only a few core particles per particle (preferably less than 1% of the particles contain more than 10 core particles). The spray product is subsequently heated in order to compress the gel to form a glass. Also in this case the addition of zinc oxide to the gel is very advantageous. The compression can be carried out at higher temperatures than with preparations to which zinc has not been added since the softening point of the glass that is formed is higher. This enables organic residues to be more easily expelled from the starting materials.

Since a preparation containing a very low proportion of particles without cores is formed in the process according to the invention, it is in general no longer necessary to subsequently fractionate particles with and without cores.

The invention also concerns a process for purifying nucleic acids by non-covalently binding nucleic acids from a sample to particles having a glass surface, removing non-bound sample components and eluting the bound nucleic acids from the glass surface wherein a preparation according to the invention is used. The process is particularly simple when the particles are magnetic.

Processes for purifying nucleic acids with the aid of magnetic particles having a glass surface are described in WO 96/41811. Reference is herewith made to the complete contents of this disclosure. Suitable samples for the purification process according to the invention are in particular clinical samples such as blood, serum, mouth rinse liquid, urine, cerebral fluid, sputum, stool, plasma, biopsy specimens or bone marrow samples. Serum is a preferred sample material. In order to purify the nucleic acids the sample, if required after lysis of cellular structures that may be present and digestion of interfering sample components, is admixed with the inventive preparation e.g. in the form of a certain amount of a particle suspension. After an incubation period during which the nucleic acids bind sequence-unspecifically to the glass surface, the liquid together with the non-bound sample components is removed and the particles are washed, if desired, in order to remove residues. The nucleic acids which are still bound thereto are removed from the surface by elution with a liquid in which the nucleic acids dissolve well. The resulting liquid can now be processed in any desired manner and in particular be used in amplification methods, e.g. PCR, since most of the enzyme inhibitors are separated during the purification process.

If the particles are magnetic, it is particularly easy to remove the liquid from the particles with the nucleic acids since the particles can be collected and held with the aid of a magnet while the liquid is removed. If the particles are non-magnetic they can be separated from the liquid by filtration using a suitable filter.

The present invention is elucidated in more detail by the following examples.

EXAMPLE 1

Sol for Preparing a Zinc-free Layer (74 $SiO_2 \times 15$ $B_2O_3$, ×4 $K_2O \times 2$ $CaO \times 5$ $Al_2O_3$)

1750 ml tetraethyl orthosilicate (manufacturer: Wacker, Burghausen) is placed in a 5 liter round bottomed flask and the following are added rapidly at room temperature while stirring (500 rpm):

541 ml triethyl borate (manufacturer: Aldrich, Steinheim)
250 ml potassium methanolate (25% in methanol (manufacturer: Fluka, Deisenhofen))
261 g aluminium sec. butylate (manufacturer: Aldrich, Steinheim)
292 ml ethanol and
8.49 g calcium (manufacturer: Fluka, Deisenhofen)

The mixture is subsequently heated to a strong reflux while stirring. A mixture of altogether 583 ml ethanol and 233 ml water is added dropwise for a period of 30 minutes. After cooling to <50° C. the sol is transferred to an open container and 1200 g of the pigment IRIODIN 600 Black Mica (manufacturer: Merck, Darmstadt) is added. After completion of the pigment addition the sol is stirred for a further 1 minute at 500 rpm and subsequently treated for 5 minutes with ultrasound. After the ultrasonic treatment the sol-pigment mixture is stirred with a dissolver stirrer at ca. 500 rpm until the entire amount is consumed.

EXAMPLE 2

Preparation of Glass-coated Pigment (MGP)

The spraying is carried out in a spray tower from the Nubilosa Company, Konstanz having a diameter of 0.75 m, a height of 2.5 m and an evaporation capacity (with reference to water) of 1–3 liters/hour. The air intake temperature is 270° C., the outlet temperature is ca. 130° C. The flow rate of air is 7.2 m³/min. A two-fluid nozzle with a spray pressure of 2 bar is used for spraying. The delivery capacity of the ball valve membrane pump is 60 g sol/min.

The spray product is captured in a cyclone, precompressed in air for 1 hour at 250° C. and subsequently brought to a temperature of 675° C. in a nitrogen oven at a heating rate of 1 K/min, kept for one hour in this oven and cooled to 300° C. Oxygen is added at 300° C., it is kept for one hour and then cooled to room temperature. After cooling it is sieved using a sieve having a mesh size of 50 µm to remove aggregates that may be present. This completes the preparation.

EXAMPLE 3

Sol for Preparing a Zinc Containing Layer (70.67 $SiO_2 \times 14.33\ B_2O_3 \times 4\ K_2O \times 2\ CaO \times 5\ Al_2O_3 \times 4\ ZnO$)

A sol containing zinc is prepared in the same manner as example 1. For this the following weights of educts are added and treated in a similar manner:

| | |
|---|---|
| 1258 ml | tetraethyl orthosilicate (manufacturer: Wacker, Burghausen) |
| 387 ml | triethyl borate (manufacturer: Aldrich, Steinheim) |
| 188 ml | potassium methanolate 25% in methanol (manufacturer: Fluka, Deisenhofen) |
| 196 g | aluminium sec. butylate (manufacturer: Aldrich, Steinheim) |
| 1285 ml | ethanol |
| 6.39 g | calcium (manufacturer: Fluka, Deisenhofen) |
| 58.5 g | zinc acetate dehydrated dihydrate (manufacturer: Fluka, Deisenhofen) |

After boiling under reflux, 178 ml $H_2O$ together with 444 ml ethanol are added dropwise within 30 minutes. After cooling 1200 g pigment is added. Otherwise refer to example 1.

EXAMPLE 4

Preparation of a Zinc-containing Glass-coated Pigment

The sol containing pigment from example 3 is processed analogously to example 2. However, the compression temperature is 750° C.

EXAMPLE 5

Preparation of Zinc-containing Glass-coated Pigment Using a Modified After-treatment (MGP, Magnetic Glass Particles)

The sol containing pigment from example 3 is processed analogously to example 2. However, the compression temperature is 750° C. and the temperature for treatment in oxygen is 200° C.

EXAMPLE 6

Determining the Yield of DNA or RNA Using Radioactive $^{32}P$ $^{32}P$-labelled HIV gag RNA standard of 1.4 kb or $^{32}P$-labelled lambda amplicons of 3 kb is used to directly detect bound or non-bound DNA or RNA. Negative plasma (human) each containing $10^9$ copies is used as the sample.
Procedure for Sample Preparation 500 µl negative plasma containing $10^9$ copies $^{32}P$-labelled lambda amplicons is placed in a 2 ml Eppendorf vessel. 480 µl binding buffer/proteinase K solution (5:1) is added by pipette, vortexed and incubated at 70° C. for 10 minutes. After cooling to room temperature, 400 µl isopropanolic MGP suspension containing a total of 3 mg MGP is added by pipette. Immediately afterwards it is mixed by vortexing. The sample is then incubated for 15 minutes on a mixer e.g. thermomixer 5436 from Eppendorf.

The MGP are concentrated by transferring the sample to a magnetic separator. After one minute the supernatant is completely removed by pipette.

0.5 ml washing buffer is added by pipette to the MGPS. The sample is vortexed and then transferred to a magnetic separator. The supernatant is removed by pipette after 1 minute. The washing procedure is repeated a further 2 times.

200 ml elution buffer is added to the MGP. They are incubated for 10 minutes at 80° C. on a thermomixer at 1400 rpm. The sample is transferred to a magnetic separator and after 1 minute the entire eluate is removed. The eluate is then transferred to a new vessel and measured in a scintillation counter.

The yield can be determined from the ratio of the radioactivity of the eluate to the radioactivity of the sample before the purification procedure.

Results with MGPs with different coatings:

| | DNA yield | RNA yield |
|---|---|---|
| MGP of example 2 (without zinc) | 44% | 44% |
| MGP of example 4 (with zinc) | 62% | 59% |
| MGP of example 6 (with zinc, modified after-treatment | 66% | 70% |

EXAMPLE 7

Black Mica (BM) as the Pigment Base (Reference Example)

A batch is manufactured according to example 1 in which the pigment is black mica (BM).

EXAMPLE 8

Microna Mat Black (MMB) as the Pigment Base

A batch is manufactured according to example 1 in which the pigment is MMB (microna mat black (manufacturer: Merck, Darmstadt).

EXAMPLE 9

Signal Level After Amplification in Which the Samples have been Prepared Using MGPs Containing Different Pigments MGPs according to example 7 and 8 are used for the sample preparation. Human plasma containing 100 copies/ml HCV viruses is used as the sample. The eluate of the sample preparation is subjected to an amplification and the amplification result is detected by an electrochemiluminescence method. In an additional experiment the sample was human plasma containing 600 copies/ml HBV viruses.

| | HCV ECL counts | HBV ECL counts |
|---|---|---|
| MGP according to example 7 (BM) | 97000 | 25000 |
| MGP according to example 8 (MMB) | 127000 | 43000 |

EXAMPLE 10

Carbonyl Iron Powder HQ as the Pigment

A zinc containing sol is prepared according to example 3 but only with 240 g sol.

After cooling 71 g carbonyl iron powder HQ (BASF, Ludwigs-hafen) with a particle size distribution of: 10%<0.5 µm, 50%<1.1 µm, 90%<2.2 µm is added, stirred for 1 minute at 500 rpm and subsequently treated with ultrasound for 5 minutes. The sol is sprayed in a spray dryer (Büche 190, Mini Spray Dryer). The nozzle temperature of the spray dryer is 140° C.

The powder obtained is heated in air at 150° C. The heating rate is 1 K/min and the holding time is 1 hour. Subsequently the air in the oven is replaced by $N_2$, flushed several times and heated at 1 K/min to 700° C., held for 1 hour, cooled to 200° C. at 1 K/min. Nitrogen is replaced by air at 200° C. and held for 1 hour. It is then cooled to room temperature. Aggregates that may have formed are removed by sieving with a 50 µm sieve.

The yield is 62.4 g. The sieve losses are negligible. Aggregates do not occur.

EXAMPLE 11

Determining the Binding of RNA $^{32}$P-labelled HIVgag standard of 1.4 kb is bound according to example 6 to the particles of example 10. The radioactivity measurement yielded a binding of >80%.

EXAMPLE 12

Comparison of the Sedimentation Rates 3 mg particles of example 10 are transferred into two Eppendorf vessels having a volume of 2 ml and suspended with 1.5 ml $H_2O$ in each case.

The particles in vessel 1 are attracted to the vessel wall with a magnet and subsequently resuspended by shaking. The particles in vessel 2 are shaken up at the same time.

Sedimentation in a gravitational field is observed visually. No differences occurred.

What is claimed is:

1. A process for producing a preparation of particles having a core coated with a gel layer containing less than 5% by weight particles without cores comprising the steps:
   suspending core particles in a sol using a core particle preparation,
   spray drying the suspension to form a gel, and
   compressing the gel to form a glass,
   wherein the core particle preparation comprises 75% by weight particles having a particle size between 0.5 and 15 µm.

2. A preparation of particles having a glass surface, comprising more than 75% by weight of these particles having a particle size between 0.5 and 15 µm, wherein more than 95% by weight of the particles having a particle size between 0.5 and 15 µm are magnetic.

3. The preparation as claimed in claim 2, wherein less than half of the particles have a particle size of less than 2 µm.

4. The preparation as claimed in claim 2, wherein less than 2% of the particles have a particle size of less than 0.5 µm.

5. The preparation as claimed in claim 2, wherein the magnetic particles have a magnetic core which is coated with glass.

6. The preparation as claimed in claim 2, wherein no more than 10% of these particles are particles with a particle size of more than 10 µm.

7. The preparation as claimed in claim 2, wherein the particles have a glass coat which contains between 2 and 6 mole % zinc oxide.

8. The preparation as claimed in claim 2, containing at least one core of a magnetic metal.

9. The preparation as claimed in claim 8, wherein the core has a particle size of between 0.01 µm and 100 µm.

10. A process for producing a preparation of particles having a core coated with a gel layer containing less than 5% by weight particles without cores comprising the steps:
    suspending core particles in a sol using a core particle preparation, and
    spray drying the suspension to form a gel,
    wherein the core particle preparation comprises 75% by weight particles having a particle size between 0.5 and 15 µm.

11. The process as claimed in claim 10, wherein the sol contains zinc.

12. A process for purifying nucleic acids by non-covalently binding nucleic acids from a sample to particles having a glass surface, removing non-bound sample components and eluting the bound nucleic acids from the glass surface, wherein the sample is contacted with a preparation as claimed in claim 2.

13. A process as claimed in claim 12, wherein the particles are magnetic and are held by a magnet while the sample components are removed.

14. The preparation as claimed in claim 9, wherein said core has a particle size of between 0.2 µm and 8 µm.

* * * * *